US006417227B1

(12) United States Patent
Lord et al.

(10) Patent No.: US 6,417,227 B1
(45) Date of Patent: Jul. 9, 2002

(54) METHODS OF DELIVERY OF CETYL MYRISTOLEATE

(75) Inventors: Gary R. Lord, Sparks; Carol D. Lytle, Reno, both of NV (US)

(73) Assignee: CG and Associates, Sparks, NV (US)

( * ) Notice: Subject to any disclaimer, the term of this patent is extended or adjusted under 35 U.S.C. 154(b) by 0 days.

(21) Appl. No.: 09/299,903

(22) Filed: Apr. 28, 1999

(51) Int. Cl.⁷ .............................................. A61K 31/215
(52) U.S. Cl. ...................................... 514/529; 424/448
(58) Field of Search ........................... 424/448; 514/529

(56) References Cited

U.S. PATENT DOCUMENTS

| | | |
|---|---|---|
| 4,049,824 A | 9/1977 | Diehl |
| 4,113,881 A | 9/1978 | Diehl |
| 5,132,115 A | 7/1992 | Wolter |
| 5,310,572 A | 5/1994 | Woodard |
| 5,393,533 A | 2/1995 | Versic |
| 5,547,683 A | 8/1996 | Yano |
| 5,569,676 A | 10/1996 | Diehl |
| 5,607,691 A | 3/1997 | Hale |
| 5,641,513 A | 6/1997 | Lech |
| 5,662,926 A | 9/1997 | Wick |
| 5,683,711 A | 11/1997 | Fischer |
| 5,801,203 A | 9/1998 | Lipton |
| 5,837,280 A | 11/1998 | Kenealy |
| 5,843,472 A | 12/1998 | Ma |
| 5,851,579 A | 12/1998 | Wu |
| 5,853,751 A | 12/1998 | Masiz |
| 5,858,393 A | 1/1999 | Bymaster |
| 5,866,157 A | 2/1999 | Higo |
| 5,876,746 A | 3/1999 | Jona |
| 5,879,702 A | 3/1999 | Sasaki |
| 5,882,675 A | 3/1999 | Ninomiya |

FOREIGN PATENT DOCUMENTS

| | | | |
|---|---|---|---|
| WO | 9826767 | * | 6/1998 |
| WO | 98/52583 | | 11/1998 |
| WO | 99/52508 | | 10/1999 |

OTHER PUBLICATIONS

International Search Report.
Cochran. Cetyl myristoleate. 1996. Healing Wisdom Publications, N.Y.
Diehl and May. 1994. J. Pharm. Sci. 83(3) 296–299.
Merkle. 1989. Meth. and Find. Exp. Clin. Pharm. 11(3):135–153.
Berner and John. 1994. Clin. Pharmacokinetics. 26(2):121–34.
Berba and Banakar. 1990. American Pharmacy. NS30(11):33–41.
Cleary. 1991. Cosmetics and Toiletries. 106:97–109.
Siemandi. 1997, Manuscript. 1–6.
Cochran and Dent. Townsend letter for doctors and patients. Jul. 1997, 70–74.
Ranade. 1991. J. Clin. Pharmacol. 31:2–16.

* cited by examiner

Primary Examiner—Michael A. Williamson
(74) Attorney, Agent, or Firm—Banner & Witcoff, Ltd.

(57) ABSTRACT

The invention provides novel and advantageous delivery devices for compositions of cetyl myristoleate. The delivery devices include transdermal delivery devices, suppositories, enteric coatings, and microencapsulation. Further provided are methods of treating diseases using the disclosed delivery devices. Diseases that can be treated with the devices include, but are not limited to, diseases associated with the inflammation of tissues, diseases associated with inflammatory conditions affecting joints, and autoimmune diseases.

12 Claims, No Drawings

METHODS OF DELIVERY OF CETYL MYRISTOLEATE

BACKGROUND OF THE INVENTION

The invention relates to novel and advantageous methods of delivery of cetyl myristoleate. The delivery methods are useful in the treatment of several diseases affecting humans and animals.

Cetyl myristoleate (CM) is found in and isolated from mice, in particular, Swiss albino mice, sperm whales, and the anal glands of some species of male beavers. The compound can also be synthesized in the laboratory using cetyl alcohol and myristoleic acid. The methods of obtaining CM are described in U.S. Pat. No. 4,049,824, 4,113,881, and 5,569,676. These patents are incorporated herein in their entirety.

CM can be used to treat diseases in humans and animals. CM is useful in the treatment of diseases associated with the inflammation of tissues such as tendinitis, tenosynovitis, bursitis, chronic patellar tendinitis, Achilles tendinitis, fibrositis, inflammation of the spine, colitis, bronchitis, polymyalagia rheumatica, Crohn's disease, primary biliary cirrhosis, pericarditis, ulcerative colitis, and Sjogren's syndrome.

CM is also useful in the treatment of inflammatory conditions that affect joints such as arthritis, juvenile chronic arthritis, chronic arthritis, Behcet's disease, ankylosing spondylitis, mixed connective tissue disease, Reiter's syndrome, and synovitis. Diehl and May, (1994) J Pharm Sci 83(3):296–299.

Autoimmune diseases such as autoimmune Addison's disease, autoimmune hepatitis, Behcet's disease, lupus, antiphospholipid syndrome, multiple sclerosis, and essential mixed cryoglobulinemia can be treated with CM.

CM can also be used in the treatment of migraine, emphysema, asthma, myofascial pain, arteriosclerosis, joint sports injuries and sprains, insulin dependant diabetes, peripheral vascular disease, carpal tunnel syndrome, cardiomyopathy, chronic fatigue immune dysfunction syndrome, Churg-Strauss syndrome, and psoriasis.

CM can be delivered orally; however, absorption of waxy esters such as CM is low compared to other lipids and is therefore very poor. The administration of lipase digestive enzyme is presently recommended along with oral doses of CM to increase absorption. New methods of delivery are needed for CM that allow for the efficient absorption of CM.

SUMMARY OF THE INVENTION

It is an object of the invention to provide transdermal delivery devices, suppositories, enterically coated compositions, and microencapsulated compositions comprising cetyl myristoleate.

It is another object of the invention to provide methods of treatment of various diseases affecting humans and animals by providing cetyl myristoleate compositions a human or animal in need thereof.

These and other objects of the invention are provided by one or more of the embodiments described below.

One embodiment of the invention provides a transdermal delivery device for the delivery of cetyl myristoleate. The transdermal delivery device contains between 1 mg and 3000 mg of cetyl myristoleate.

Another embodiment of the invention provides for a transdermal delivery device comprising a backing layer and a matrix layer underlying the backing layer. The matrix layer of the transdermal delivery device comprises a mixture of cetyl myristoleate and a pressure sensitive adhesive.

Even another embodiment of the invention provides a transdermal delivery device wherein the matrix layer further comprises one or more of the components selected from the group consisting of glucosamine sulfate, chondroitin sulfate, sea cucumber extract, hydrolyzed shark cartilage, collagen II, and methylsulfonylmethane.

Still another embodiment of the invention provides a transdermal delivery device wherein the device is worn for between 5 and 10 days.

Yet another embodiment of the invention provides a transdermal delivery device wherein between 0.01 mg/kg/day and 10 mg/kg/day of cetyl myristoleate is delivered.

A further embodiment of the invention provides a method of treating a disease associated with the inflammation of tissues. A transdermal delivery device comprising cetyl myristoleate is affixed to the skin of an animal or human. The transdermal delivery device is useful in treating diseases selected from the group consisting of tendinitis, tenosynovitis, bursitis, chronic patellar tendinitis, Achilles tendinitis, fibrositis, inflammation of the spine, colitis, bronchitis, polymyalagia rheumatica, Crohn's disease, primary biliary cirrhosis, pericarditis, ulcerative colitis, and Sjogren's syndrome.

Another embodiment of the invention provides a method of treating a disease associated with an inflammatory condition that affects joints. A transdermal device comprising cetyl myristoleate is affixed to the skin of an animal or human. The disease to be treated is selected from the group consisting of arthritis, chronic arthritis, Behcet's disease, ankylosing spondylitis, mixed connective tissue disease, Reiter's syndrome and synovitis.

Even another embodiment of the invention provides a method of treating an autoimmune disease. A transdermal device comprising cetyl myristoleate is affixed to the skin of an animal or human. The disease to be treated is selected from the group consisting of autoimmune Addison's disease, autoimmune hepatitis, Behcet's disease, lupus, antiphospholipid syndrome, multiple sclerosis, and essential mixed cryoglobulinemia.

Still another embodiment of the invention provides an oral medicament comprising cetyl myristoleate and an enteric coating. The enteric coating is resistant to dissolution in the stomach but predisposed to dissolution in the intestine so as to prevent release of the cetyl myristoleate until the medicament is in the intestine.

Yet another embodiment of the invention provides for an oral medicament comprising cetyl myristoleate and an enteric coating. The enteric coating is resistant to dissolution in an environment having a pH less than 5.5.

A further embodiment of the invention provides for an oral medicament comprising cetyl myristoleate and an enteric coating. The oral medicament comprises between 0.1 g and 1 g of cetyl myristoleate.

Another embodiment of the invention provides an oral medicament comprising cetyl myristoleate and an enteric coating. The oral medicament further comprises one or more of the components selected from the group consisting of glucosamine sulfate, chondroitin sulfate, sea cucumber extract, hydrolyzed shark cartilage, collagen II, and methylsulfonylmethane.

Even another embodiment of the invention provides a method of treating a disease associated with the inflammation of tissues. An oral medicament comprising cetyl myristoleate and an enteric coating is administered to a human or animal. The disease to be treated is selected from the group consisting of tendinitis, tenosynovitis, bursitis, chronic patellar tendinitis, Achilles tendinitis, fibrositis, inflammation of the spine, colitis, bronchitis, polymyalagia rheumatica, Crohn's disease, primary biliary cirrhosis, pericarditis, ulcerative colitis, and Sjogren's syndrome.

Still another embodiment of the invention provides for a method of treating a disease associated with an inflammatory condition that affects joints. An oral medicament comprising cetyl myristoleate and an enteric coating is administered to a human or animal. The disease to be treated is selected from the group consisting of arthritis, chronic arthritis, Behcet's disease, ankylosing spondylitis, mixed connective tissue disease, Reiter's syndrome, and synovitis.

Yet another embodiment of the invention provides for a method of treating an autoimmune disease. An oral medicament comprising cetyl myristoleate and an enteric coating is administered to a human or animal. The disease to be treated is selected from the group consisting of autoimmune Addison's disease, autoimmune hepatitis, Behcet's disease, lupus, antiphospholipid syndrome, multiple sclerosis, and essential mixed cryoglobulinemia.

A further embodiment of the invention provides an oral medicament comprising microencapsulated cetyl myristoleate. The microencapsulation is resistant to dissolution in the stomach but predisposed to dissolution in the intestine so as to prevent release of the cetyl myristoleate until the medicament is in the intestine.

Another embodiment of the invention provides for an oral medicament comprising microencapsulated cetyl myristoleate. The oral medicament comprises between 0.1 g and 1 g of cetyl myristoleate.

Even another embodiment of the invention provides for an oral medicament comprising microencapsulated cetyl myristoleate The oral medicament further comprises one or more of the components selected from the group consisting of glucosamine sulfate, chondroitin sulfate, sea cucumber extract, hydrolyzed shark cartilage, collagen II, and methylsulfonylmethane.

Still another embodiment of the invention provides for a method of treating a disease associated with the inflammation of tissues. An oral medicament comprising microencapsulated cetyl myristoleate is administered to a human or animal. The disease to be treated is selected from the group consisting of tendinitis, tenosynovitis, bursitis, chronic patellar tendinitis, Achilles tendinitis, fibrositis, inflammation of the spine, colitis, bronchitis, polymyalagia rheumatica, Crohn's disease, primary biliary cirrhosis, pericarditis, ulcerative colitis, and Sjogren's syndrome.

Yet another embodiment of the invention provides for a method of treating a disease associated with an inflammatory condition that affects joints. An oral medicament comprising microencapsulated cetyl myristoleate is administered to a human or animal. The disease to be treated is selected from the group consisting of arthritis, chronic arthritis, Behcet's disease, ankylosing spondylitis, mixed connective tissue disease, Reiter's syndrome, and synovitis.

A further embodiment of the invention provides for a method of treating an autoimmune disease. An oral medicament comprising microencapsulated cetyl myristoleate is administered to a human or animal. The disease to be treated is selected from the group consisting of autoimmune Addison's disease, autoimmune hepatitis, Behcet's disease, lupus, antiphospholipid syndrome, multiple sclerosis, and essential mixed cryoglobulinemia Another embodiment of the invention provides for a suppository for transrectal or transurethral delivery. The suppository comprises cetyl myristoleate in combination with a physiologically acceptable solid carrier that is meltable at human or animal body temperature.

Even another embodiment of the invention provides for a suppository comprising between 1 mg and 3000 mg of cetyl myristoleate.

Still another embodiment of the invention provides for a suppository comprising cetyl myristoleate. The suppository further comprising one or more of the components selected from the group consisting of glucosamine sulfate, chondroitin sulfate, sea cucumber extract, hydrolyzed shark cartilage, collagen II, and methylsulfonylmethane Yet another embodiment of the invention provides a method for treating a disease associated with the inflammation of tissues. A suppository comprising cetyl myristoleate is administered to a human or animal. The disease to be treated is selected from the group consisting of tendinitis, tenosynovitis, bursitis, chronic patellar tendinitis, Achilles tendinitis, fibrositis, inflammation of the spine, colitis, bronchitis, polymyalagia rheumatica, Crohn's disease, primary biliary cirrhosis, pericarditis, ulcerative colitis, and Sjogren's syndrome.

A further embodiment of the invention provides for a method of treating a disease associated with an inflammatory condition that affects joints. A suppository comprising cetyl myristoleate is administered to a human or animal. The disease to be treated is selected from the group consisting of arthritis, chronic arthritis, Behcet's disease, ankylosing spondylitis, mixed connective tissue disease, Reiter's syndrome, and synovitis.

Another embodiment of the invention provides for a method of treating an autoimmune disease. A suppository comprising cetyl myristoleate is administered to a human or animal. The disease to be treated is selected from the group consisting of autoimmune Addison's disease, autoimmune hepatitis, Behcet's disease, lupus, antiphospholipid syndrome, multiple sclerosis, and essential mixed cryoglobulinemia.

DESCRIPTION OF THE INVENTION

Cetyl myristoleate (CM) is a fatty acid ester of the following structure:

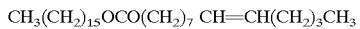

$$CH_3(CH_2)_{15}OCO(CH_2)_7\ CH{=}CH(CH_2)_3CH_3$$

The invention provides novel methods of delivery of CM such that good absorption of the drug is achieved. These methods include transdermal delivery devices, suppositories, enteric coatings, and microencapsulation.

The transdermal delivery devices of this invention are matrix or monolithic-type laminated structures. Such transdermal delivery devices are well known in the art. Cleary, Cosmetics and Toiletries, (1991) 106:97–109. Transdermal delivery devices comprise a matrix layer of the drugs, enhancer, or other components of the pharmaceutical composition admixed with a pressure sensitive adhesive and a backing layer. The matrix serves as a reservoir for the drugs and as the means of affixing the transdermal delivery devices to the skin. Alternatively, the adhesive can be provided in a layer separate from the matrix. The transdermal delivery devices preferably comprise a release liner layer that is removed prior to use.

The virtually impermeable backing layer provides the top face of the transdermal delivery device and is the side furthermost away from the skin. The backing layer protects the transdermal delivery device and prevents the escape of the drug, adhesive, enhancer or other components of the pharmaceutical composition contained within the transdermal delivery device.

The backing layer is preferably made of a material that is inert and incapable of absorbing the drug, adhesive, enhancer, or other components of the pharmaceutical composition contained within the transdermal delivery device. The backing layer may be comprised of dermatologically acceptable films such as polyesters, polyurethanes, polyethylenes, polypropylenes, polyether amides, polyvinylchloride, polyvinylidene chloride, polyolefins, rubbers, synthetic resins, cloth, foils, and various laminates of these materials. This layer may be pigmented, metallized, or provided with a matte finish suitable for writing. The backing layer may be occlusive (impermeable to gases and liquids) providing for skin hydration, or non-occlusive (allowing moisture to pass through) providing for less skin hydration.

An adhesive layer is used to achieve contact between the transdermal delivery device and skin. Preferably, the adhesive layer provides instantaneous adhesion of the transdermal delivery device to the skin while allowing for easy removal from the skin. The matrix layer can contain a pressure sensitive adhesive. Alternatively, an adhesive layer can be independent of the matrix layer. Materials used in pressure sensitive adhesives include, but are not limited to natural rubber, styrene-butadiene-rubber polymers, styrene-butadiene-styrene or styrene-isoprene block copolymers, polyisoprene, polyisobutylene, butyl rubber, polyacrylates, silicone pressuresensitive adhesives, polyisobutylene, and vinyl ether polymers.

The matrix layer contains the drug and may also contain adhesive, enhancer, or other components of the pharmaceutical composition. The most simple transdermal delivery device design comprises the incorporation of the drug into a adhesive matrix covering the backing layer. The drug may be dissolved or dispersed in the adhesive matrix, or bound to a non-soluble absorbent in the adhesive matrix. Alternatively, a porous pad soaked with an adhesive gel or liquid containing the drug can be used.

The matrix may include other additives depending upon the particular adhesive and drug used. For example, polyvinyl pyrrolidone (PVP) which inhibits drug crystallization, hygroscopic agents that improve the duration of wear, or additives that improve the physical (e.g cold flow) or adhesive (e.g. tack cohesive strength) properties of the matrix can be added.

The matrix may also be non-adhesive. The non-adhesive matrix comprises the drug, enhancer or other components of the pharmaceutical composition dissolved or dispersed in a matrix or bound to a non-soluble absorbent in the matrix. Suitable matrix materials include, but are not limited to, polysaccharides such as starch, cellulose, hyaluronic acid, pectin, seaweed gums, polypeptides such as casein, albumin, keratin and collagen, thermoplastics such as unvulcanized elastomers, nylon, polyethylene, polyurethane, acrylic resins, cellulose resins, polypropylene, polyethylene glycols, polyvinylacetates, polyvinyl alcohols, and polyvinylpyrrolidones. In these peripheral adhesive systems the non-adhesive matrix is lined with a separate adhesive layer. The peripheral adhesive system may also comprise a porous pad filled with non-adhesive gel or liquid and equipped with peripheral adhesive.

Additionally, in contrast to homogeneous bulk concentrations of the drug in the matrix, a bulk concentration gradient of the drug may be established. Such gradients comprise drug adsorbents located in the deeper layers of the matrix only. The gradients provide for uniform release rates.

The transdermal delivery device may include a release liner or peel strip. The release liner covers the surface of the adhesive during storage and protects the adhesive and matrix, and maintains drug stability. The release liner may be made from any impermeable film including, but not limited to, those materials specified for the backing layer. Preferably, the release layer is comprised of silicone-coated polyester.

The transdermal delivery device may further be comprised of permeability enhancers to improve the permeability of the skin. Such compounds include, but are not limited to dimethylsulfoxide, dimethylformamide, decylmethylsulfoxide, 2-pyrrolidone, N-methyl-2-pyrrolidone, 1-dodecylazacylcloheptan-2-one, propylene glycol, oleic acid, lactate ester of $C_{12}C_{18}$ aliphatic alcohol, lauryl lactate, N,N-dimethylacetamide, polyethylene glycol monolaurate, glycerol monolaurate, lecithin, and sodium laurylsulfate. The amount of permeation enhancer included in the matrix will depend upon the particular enhancer or enhancers used, the strength of the enhancer, the desired increase in skin permeability, and the amount of drug to be delivered. In most cases the enhancer will constitute in the range of 1 to 20% by weight of the matrix.

The transdermal delivery devices of the invention may be fabricated using procedures known in the transdermal delivery devices art. In general, the matrix is formulated (i.e. the adhesive, drug(s), permeation enhancer, and any additives are mixed). The matrix is coated on the backing or release liner layer, the solvent is removed from the matrix, and the backing or release layer is added.

The transdermal delivery devices can be fabricated using conventional coating and laminating techniques and equipment which are known to those skilled in the art. Transdermal delivery devices can be fabricated by techniques including, but not limited to, solvent evaporation film casting, melt extrusion, thin film lamination, and die cutting.

CM may also be delivered via a transrectal or transurethral suppository. Typical carriers used in standardized suppositories are solid and meltable at human or animal body temperature. Examples of carriers include, but are not limited to, beeswax or glycerol or both.

Other components that may be included in the transdermal delivery device and suppository CM drug formulations of the invention include carriers such as water, azone, and propylene glycol, tackifers, pigments, dyes, and other additives that do not adversely affect the mechanical or adhesive properties of the formulation.

The amount of CM incorporated in a transdermal delivery device will vary depending upon on the dosage required, the permeability of the pressure-sensitive adhesive materials, the thickness of the pressure-sensitive adhesive layer, and the length of time the transdermal delivery device is to remain on the skin. The amount of CM incorporated in a suppository will vary depending upon the dosage of CM required.

The transdermal delivery device or suppository may contain between 1 mg and 3000 mg of CM, preferably, the transdermal delivery device contains between 1 mg and 1000 mg of CM, more preferably the transdermal delivery device contains between 200 mg and 600 mg of CM, more preferably the transdermal delivery device contains between 300 mg and 500 mg of CM. When CM is administered by transdermal delivery device or suppository, the effective therapeutic dose is normally in the range of 0.01 mg/kg/day to about 10 mg/kg/day, preferably, from 0.1 mg/kg/day to about 5 mg/kg/day, preferably from 0.2 mg/kg/day to about 1.0 mg/kg/day, and more preferably from 0.4 mg/kg/day to about 0.8 mg/kg/day. These rates may vary depending upon the symptom or symptoms being treated.

The transdermal delivery device may be worn for a period of time ranging from between a few hours to 15 days, preferably the transdermal delivery device is worn for 3 to 15 days, more preferably the transdermal delivery device is worn for 5–10 days. The length of treatment may vary depending upon the symptom or symptoms being treated. The transdermal delivery devices of the invention will preferably have a basal surface area of between 10 and 50 cm$^2$; however, the surface area may be smaller or larger.

Where suppositories are used to deliver CM the length of treatment will range from 5 days to 30 days, more preferably, the length of treatment will range from 7 to 20 days, more preferably the length of treatment will range from 10–15 days. The length of treatment may vary depending upon the symptom or symptoms being treated.

The transdermal delivery device or suppository may also contain glucosamine sulfate, glucosamine hydrochloride, chondroitin sulfate, sea cucumber extract, hydrolyzed shark cartilage, collagen II, and methylsulfonylmethane. Preferably, the amounts of each of these ingredients range from between 1000 mg and 10 mg, preferably, the amounts of each of these ingredients range from between 750 mg and 50 mg, even more preferably, the amounts of each of these ingredients range from between 500 mg and 100 mg.

The transdermal delivery device or suppository may also contain herbal ingredients. Preferably, the herbal ingredients are listed on the USDA GRAS list. Examples of such herbal ingredients include, but are not limited to, licorice root, cat's claw, black cohosh root, boswellia herb, curcumin, ginger root, cinnamon bark, and bromelain. The amount of each of the herbal ingredients ranges from between 150 mg and 5 mg, preferably the amount of each of the herbal ingredients ranges from between 100 mg and 10 mg, even more preferably the amount of each of the herbal ingredients ranges from 75 mg to 20 mg.

The transdermal delivery device or suppository may also contain vitamins or minerals, including, but not limited to, zinc, magnesium, and manganese.

Glucosamine sulfate, chondroitin sulfate, sea cucumber extract, hydrolyzed shark cartilage, collagen II, methylsulfonylmethane, herbal ingredients, vitamins and minerals may also be administered orally along with the CM transdermal delivery device or CM suppositories.

Another aspect of the invention provides for the oral administration of CM such that the drug is released when it reaches the small intestine. Release of CM into the small intestine is desirable because significantly better absorption of CM occurs in the small intestine as compared to the stomach. CM may be delivered to the small intestine using an enteric coating or microencapsulation.

Enteric coatings are used to deliver drugs to the small intestine and to protect drugs from inactivation by gastric enzymes or low pH. Targeted delivery is based upon the pH differences between these two parts of the alimentary canal. Enteric coatings are selectively insoluble substances that are insoluble in a low pH medium typically having a value less than about 5.5, but are soluble in a higher pH medium typically having a value greater than about 5.5.

The coatings provide an impermeable barrier which will not readily dissolve or disperse at the low pH of the gastric juices of the stomach. However, at the higher pH of the intestinal fluids the enteric coating will dissolve or disperse allowing for absorption of the drug.

CM is provided in an enterically coated, delayed release formulation. To prepare the delayed release enterically coated formulations of CM, pharmaceutical preparations of CM are either formed into a tablet or put into a capsule, and the tablet or capsule is coated with an enteric-coating material which dissolves at a pH of approximately 5.5 or greater. Suitable materials for enteric coatings include, but are not limited to methacrylic acid copolymers, cellulose acetate phthalate, cellulose acetate succinate, and styrol maleic acid co-polymers, polymethacrylic acid/acrylic acid copolymer, hydroxypropyl methyl cellulose phthalate, polyvinyl acetate phthalate, hydroxyethyl ethyl cellulose phthalate, hydroxypropyl methyl cellulose acetate succinate, cellulose acetate tetrahydrophtalate, acrylic resin, cellulose acetate, timellitate, and phthalate or polyphthalate esters of film-forming polymers such as those listed above. The choice of enteric-coating material is not of significance as long as release is delayed until the formulation reaches the small intestine.

To apply an enteric coating onto a dosage form substrate an organic solvent may be used as a vehicle for coating the polymers. Examples of organic solvents include acetone, methanol, ethanol, isopropyl alcohol, ethyl acetate, methylene chloride, or mixtures thereof. Aqueous coating systems such as acrylic enteric polymers in latex form, aqueous dispersions of cellulosic enteric polymers and aqueous ammonium salt solutions of cellulosic enteric polymers may also be used. The coating may be applied by spray coating, fluid bed coating, chemical vapor deposition, rotating pan coating, coascervation tank or any other process known in the art.

The formulations of the present invention may also be encapsulated in other time-release delivery systems such as a liposome delivery system, polysaccharides exhibiting a slow release mechanism, salistic or other polymer implants or microspheres. In these time release delivery systems, the active compound is suitably protected with differentially degradable coatings, e.g., by microencapsulation and multiple coatings, and such means effect continual dosing of compositions contained therein.

CM can also be coated by microencapsulation to provide for release in the small intestine instead of the stomach. Microencapsulation advantageously provides for better absorption of CM, taste abatement, and GI tolerability. Coacervation can be used to microencapsulate a drug. In coacervation, a hydrophilic substance is added to a solution of colloid. Ranade, Drug Delivery Systems 5A, (1991) J Clin Pharmacol 31:2–16. If a drug is sensitive to water it may still be microencapsulated by protecting the drug from the aqueous environment by coating the drug with polymers such as ethylcellulose, cellulose acetate phthalate, or carnauba wax prior to microencapsulation. CM may also be microencapsulated by spray coating, fluid bed coating, chemical vapor deposition, rotating pan coating, or any other process know in the art.

Hydrophilic or hydrophobic substances or mixtures thereof may be used in microencapsulation. Natural polymers such as starch and other polysaccharides can be employed as well as synthetic polymers and phospholipids. Other materials suitable for use in microencapsulation include, but are not limited to, methacrylic acid ester copolymers, polysaccharides and their derivatives of natural or synthetic origin, cellulose derivatives including, but not limited to chitin derivatives, polymers of $\alpha$ and/or $\beta$-hydroxycarboxylic acids, polymers of glycolic acid, polymers of lactic acid, polymers of $\alpha$-hydroxybutyric acid, polymers of $\alpha$-hydroxyvaleric acid and/or their copolymers, or mixtures of such polymers and/or copolymers. Further, enteric coatings may be used in microencapsulation.

The thickness of the microencapsulation coat can be adjusted from less than 1 μm to 200 μm by changing the amount of coating material. The microencapsulated drug may also be admixed or concentrically coated with other fractions of free or time-released drug. The admixtures may be placed in either capsules or tablets and with other ingredients such as binders, fillers, and lubricants.

When CM is administered with an enteric coating or by microencapsulation, the effective dose is normally in the range of 0.1 g/kg/day to about 1 g/kg/day, preferably from 0.1 g/kg/day to about 0.5 g/kg/day, and more preferably from 0.15 g/kg/day to about 0.25 g/kg/day. The length of treatment will range from 5 days to 30 days, more preferably, the length of treatment will range from 7 to 20 days, more preferably the length of treatment will range from 10–15 days. The dosage and length of treatment may vary depending upon the symptom or symptoms being treated.

EXAMPLES

Example 1

The transdermal delivery devices of the invention can be tested using the epidermal layers of human cadaver skin. Skin flux ($\mu g/cm^2/hr$) may be determined from the steady-state slope of the plot of the cumulative amount of CM permeated through the skin versus time.

The transdermal delivery devices and suppositories of the invention may further be tested by obtaining blood samples from healthy adult volunteers. A transdermal delivery device or suppository containing CM may be administered to the volunteers. Blood is collected at 1, 2, 4, 6, 8, 10, 14, 22 and 24 hours after application of the CM transdermal delivery device or suppositories. The transdermal delivery device is then removed from the skin of the volunteers. The amount of CM in the blood is determined by thin layer chromatography (TLC). One week later, the same volunteers are given CM by mouth. Blood is collected from the volunteers before the oral delivery and at 1, 2, 4, 6, 8, 10, 14, 22, and 24 hours after delivery. The amount of CM in the blood is determined by TLC and is compared to the blood levels of CM delivered by the transdermal delivery device.

Example 2

The microencapsulated and enterically coated CM compositions of the invention may be tested by obtaining blood samples from healthy adult volunteers. A dose of the microencapsulated or enterically coated CM compositions are administered to the volunteers and blood is collected at 1, 2, 4, 6, 8, 10, 14, 22 and 24 hours after administration. The amount of CM in the blood is determined by thin layer chromatography (TLC). One week later, the same volunteers are given oral doses of the same CM compositions; however, these CM compositions are not microencapsulated or enterically coated. Blood is collected from the volunteers before the oral delivery and at 1, 2, 4, 6, 8, 10, 14, 22, and 24 hours after delivery. The amount of CM in the blood is determined by TLC and is compared to the blood levels of CM delivered by microencapsulated and enterically coated CM compositions.

What is claimed is:

1. A method of treating a disease associated with the inflammation of tissues comprising administering to a human or animal an oral medicament comprising cetyl myristoleate and an enteric coating, said coating being resistant to dissolution in the stomach but predisposed to dissolution in the intestine, wherein said disease is selected from the group consisting of tendinitis, tenosynovitis, bursitis, chronic patellar tendinitis, Achilles tendinitis, fibrositis, inflammation of the spine, colitis, bronchitis, polymyalgia rheumatica, Crohn's disease, primary biliary cirrhosis, pericarditis, ulcerative colitis, and Sjogren's syndrome.

2. The method of claim 1, wherein said enteric coating is resistant to dissolution in an environment having a pH less than about 5.5.

3. The method of claim 1, wherein said oral medicament comprises between 0.1 g and 1 g of cetyl myristoleate.

4. The method of claim 1, wherein said oral medicament further comprises one or more of the components selected from the group consisting of glucosamine sulfate, chondroitin sulfate, sea cucumber extract, hydrolyzed shark cartilage, collagen II, and methylsulfonylmethane.

5. A method of treating a disease associated with an inflammatory condition that affects joints comprising administering to a human or animal an oral medicament comprising cetyl myristoleate and an enteric coating, said coating being resistant to dissolution in the stomach but predisposed to dissolution in the intestine, wherein said disease is selected from the group consisting of arthritis, chronic arthritis, Behcet's disease, ankylosing spondylitis, mixed connective tissue disease, Reiter's syndrome, and synovitis.

6. The method of claim 5, wherein said enteric coating is resistant to dissolution in an environment having a pH less than about 5.5.

7. The method of claim 5, wherein said oral medicament comprises between 0.1 g and 1 g of cetyl myristoleate.

8. The method of claim 5, wherein said oral medicament further comprises one or more of the components selected from the group consisting of glucosamine sulfate, chondroitin sulfate, sea cucumber extract, hydrolyzed shark cartilage, collagen II, and methylsulfonylmethane.

9. A method of treating an autoimmune disease comprising a administering to a human or animal an oral medicament comprising cetyl myristoleate and an enteric coating, said coating being resistant to dissolution in the stomach but predisposed to dissolution in the intestine, wherein said disease is selected from the group consisting of autoimmune Addison's disease, autoimmune hepatitis, Behect's disease, lupus, antiphospholipid syndrome, multiple sclerosis, and essential mixed cryoglobulinemia.

10. The method of claim 9, wherein said enteric coating is resistant to dissolution in an environment having a pH less than about 5.5.

11. The method of claim 9, wherein said oral medicament comprises between 0.1 g and 1 g of cetyl myristoleate.

12. The method of claim 9, wherein said oral medicament further comprises one or more of the components selected from the group consisting of glucosamine sulfate, chondroitin sulfate, sea cucumber extract, hydrolyzed shark cartilage, collagen II and methylsulfonylmethane.

* * * * *